US00PP33807P2

(12) United States Plant Patent
Hurley

(10) Patent No.: US PP33,807 P2
(45) Date of Patent: Jan. 4, 2022

(54) BUDDLEJA PLANT NAMED 'BUDHUR99'

(50) Latin Name: *Buddleia davidii*
Varietal Denomination: BUDHUR99

(71) Applicant: Judy Hurley, Stourport on Severn (GB)

(72) Inventor: Judy Hurley, Stourport on Severn (GB)

( * ) Notice: Subject to any disclaimer, the term of this patent is extended or adjusted under 35 U.S.C. 154(b) by 0 days.

(21) Appl. No.: 17/222,693

(22) Filed: Apr. 5, 2021

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ..... A01H 5/02; A01H 6/00
See application file for complete search history.

*Primary Examiner* — Keith O. Robinson
(74) *Attorney, Agent, or Firm* — C. Anne Whealy

(57) ABSTRACT

A new and distinct cultivar of *Buddleja* plant named 'BUDHUR99', characterized by its upright and outwardly spreading plant habit; moderately vigorous growth habit; freely branching habit; dense and bushy appearance; durable variegated leaves that resist scorching under full sunlight conditions; narrow conical inflorescences with numerous light purple-colored flowers that are sterile; and good garden performance and winter hardiness.

1 Drawing Sheet

Botanical designation: *Buddleia davidii.*
Cultivar denomination: 'BUDHUR99'.

STATEMENT REGARDING PRIOR DISCLOSURES BY INVENTOR/APPLICANT

The Inventor/Applicant assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct *Buddleja* plant, botanically known as *Buddleja davidii* and hereinafter referred to by the name 'BUDHUR99'.

The new *Buddleja* plant originated from an open-pollination in 1999 in an outdoor nursery in Solihul, United Kingdom of an unnamed selection of *Buddleja davidii*, not patented, as the female, or seed, parent with an unknown selection of *Buddleja davidii* as the male, or pollen, parent. The new *Buddleja* plant was discovered and selected by the Inventor as a single plant within the progeny of the stated open-pollination in a controlled outdoor environment in Solihul, United Kingdom in 1999.

Asexual reproduction of the new *Buddleja* plant by softwood stem cuttings in a controlled greenhouse environment in Bressingham, United Kingdom since September, 2009 has shown that the unique features of this new *Buddleja* plant are stable and reproduced true to type in successive generations.

SUMMARY OF THE INVENTION

Plants of the new *Buddleja* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BUDHUR99'. These characteristics in combination distinguish 'BUDHUR99' as a new and distinct *Buddleja* plant:

1. Upright and outwardly spreading plant habit.
2. Moderately vigorous growth habit.
3. Freely branching habit; dense and bushy appearance.
4. Durable variegated leaves that resist scorching under full sunlight conditions.
5. Narrow conical inflorescences with numerous light purple-colored flowers that are sterile.
6. Good garden performance and winter hardiness.

Plants of the new *Buddleja* differ primarily from plants of the female parent selection in foliage color as plants of the new *Buddleja* have variegated leaves whereas plants of the female parent selection have non-variegated leaves.

Plants of the new *Buddleja* can be compared to plants of *Buddleja davidii* 'Summer Skies', disclosed in U.S. Plant Pat. No. 22,465. In side-by-side comparisons, plants of the new *Buddleja* differ primarily from plants of 'Summer Skies' in the following characteristics:

1. Plants of the new *Buddleja* are more outwardly spreading than plants of 'Summer Skies'.
2. Leaves of plants of the new *Buddleja* are variegated whereas leaves of plants of 'Summer Skies' are not variegated and are bright yellow in color.
3. Plants of the new *Buddleja* flower later than plants of 'Summer Skies'.
4. Plants of the new *Buddleja* are not as freely flowering as plants of 'Summer Skies'.
5. Flowers of plants of the new *Buddleja* are light purple in color whereas flowers of plants of 'Summer Skies' are pale violet blue in color.

BRIEF DESCRIPTION OF THE PHOTOGRAPHS

The accompanying colored photographs illustrate the overall appearance of the new *Buddleja* plant showing the colors as true as it is reasonably possible to obtain in colored reproductions of this type. Colors in the photographs may differ slightly from the color values cited in the detailed botanical description which accurately describe the colors of the new *Buddleja* plant.

The photograph is a side perspective view of a typical flowering plant of 'BUDHUR99' grown in an outdoor nursery.

DETAILED BOTANICAL DESCRIPTION

The following observations, measurements and values describe plants grown during the mid to late summer in containers in an outdoor nursery in Fort Worth, Tex. and under cultural practices typical of commercial *Buddleja* production. Plants were two years old when the description were taken. Plants used for the photographs were grown in an outdoor nursery in Lancaster, Pa. during the late summer. Plants were five years old when the photographs were taken. In the following description, color references are made to The Royal Horticultural Society Colour Chart, 2015 Edition, except where general terms of ordinary dictionary significance are used.

Botanical classification: *Buddleja davidii* 'BUDHUR99'.

Parentage:

*Female, or seed, parent*.—Unnamed selection of *Buddleja davidii*, not patented.

*Male, or pollen, parent*.—Unknown selection of *Buddleja davidii*, not patented.

Propagation:

*Type*.—By softwood stem cuttings.

*Time to initiate roots plant, summer*.—About ten weeks at soil temperatures about 15° C. and ambient temperatures about 22° C.

*Time to produce a rooted plant, summer*.—About 90 days at soil temperatures about 15° C. and ambient temperatures about 22° C.

*Root description*.—Fine to medium in thickness, fibrous; close to 158B in color, actual color of the roots is dependent on substrate composition, water quality, fertilizer, substrate temperature and physiological age of roots.

*Rooting habit*.—Freely branching; medium density.

Plant description:

*Plant and growth habit*.—Deciduous perennial shrub; upright and outwardly spreading plant habit; freely branching habit, dense and bushy appearance; moderately vigorous growth habit and moderate growth rate.

*Plant height*.—About 15 cm.

*Plant width* (*spread*).—About 36 cm.

*Lateral branches*.—Quantity: Freely branching habit with about twelve primary lateral branches developing per plant with secondary lateral branches developing potentially at every node. Length: About 17 cm. Diameter: About 3 mm. Internode length: Relatively short, about 2 cm. Strength: Strong, flexible. Aspect: Initially upright to about 45° from vertical; with subsequent development, close to horizontal. Texture and luster: Initially, soft pubescent, then becoming glabrous and woody with development; matte. Color, developing: Close to 144A; pubescence, close to 196A to 196B. Color, woody: Close to 199A.

Leaf description:

*Arrangement and appearance*.—Opposite, simple.

*Length*.—About 4 cm.

*Width*.—About 1.6 cm.

*Shape*.—Elliptic.

*Apex*.—Narrowly acute.

*Base*.—Cuneate to attenuate.

*Margin*.—Serrate; undulate.

*Texture and luster, upper and lower surfaces*.—Smooth, glabrous; rugose; matte.

*Venation pattern*.—Pinnate.

*Color*.—Developing and fully expanded leaves, upper surface: Center, close to 147A; surrounding center and to the margins, close to 154D; venation, similar to lamina. Developing and fully expanded leaves, lower surface: Center, close to 191A; surrounding center and to the margins, close to 11D; venation, similar to lamina.

*Petioles*.—Length: About 5 mm. Diameter: About 2 mm. Texture and luster, upper and lower surfaces: Smooth, glabrous; matte. Strength: Moderately strong, flexible. Color, upper surface: Close to 154D. Color, lower surface: Close to 11D.

Flower description:

*Flower type and flowering habit*.—Single salverform flowers arranged on terminal panicles; inflorescences face mostly outwardly; panicles long and conical in shape; freely flowering habit with more than 150 flowers developing per inflorescence and about 10 to 15 inflorescences in flower at one time; flowers face upright, outwardly to downward depending on position on the panicle; flowers persistent.

*Fragrance*.—Faintly fragrant; sweet and pleasant.

*Natural flowering season*.—Long flowering period, plants flower continuously from early August into the early autumn in Texas.

*Flower buds*.—Height: About 8 mm. Diameter: About 1.5 mm. Shape: Narrowly ovoid. Color: Close to N82B to N82C.

*Inflorescence length*.—About 12 cm.

*Inflorescence diameter*.—About 3.75 cm.

*Flower diameter*.—About 5 mm.

*Flower depth* (*height*).—About 7.5 mm to 9 mm.

*Throat diameter*.—About 1 mm.

*Tube length*.—About 5 mm.

*Tube diameter, proximally*.—About 1 mm.

*Petals*.—Quantity per flower: Typically four in a single whorl fused at the base. Length: About 2.5 mm. Width: About 3 mm. Shape: Oblong to obovate. Apex: Obtuse. Margin: Entire; slightly undulate. Texture and luster, upper and lower surfaces: Smooth, glabrous; matte. Color: Developing and fully expanded petals, upper surface: Close to N82C; venation, close to N82C; color becoming closer to N82D with development. Developing and fully expanded petals, lower surface: Close to N82D; venation, close to N82D; color does not change with development. Throat: Close to 15A. Tube: Close to 85B to 85C.

*Sepals*.—Quantity per flower: Typically four in a single whorl. Length: About 1 mm. Width: Less than 1 mm. Shape: Narrowly ovate to lanceolate. Apex: Acute. Base: Fused at the base. Margin: Entire. Texture, upper and lower surfaces: Smooth, glabrous. Color, upper surface: Close to 145A. Color, lower surface: Close to 143A.

*Peduncles*.—Length: About 5 mm. Diameter: About 1 mm. Strength: Strong. Angle: Upright to outwardly. Texture: Slightly pubescent. Color: Close to 144A to 144B.

*Pedicels*.—Length: About 1.5 mm. Diameter: Less than 1 mm. Strength: Strong. Angle: Outwardly. Texture: Slightly pubescent. Color: Close to 144A to 144B.

*Reproductive organs*.—Stamens: Quantity per flower: Typically four. Filament length: About 0.5 mm. Filament color: Close to 27D. Anther length: About 1 mm. Anther shape: Oblong. Anther color: Close to 157B. Pollen amount: None observed. Pistils: Quantity per flower: One. Pistil length: About 1 mm. Stigma shape: Oblong. Stigma color: Close to 144A to 144B.

*Seeds and fruits*.—To date, seed and fruit development have not been observed on plants of the new *Buddleja*.

Pathogen & pest resistance: To date, plants of the new *Buddleja* have not been observed to be resistant to pathogens and pests common to *Buddleja* plants.

Garden performance: Plants of the new *Buddleja* have been observed to have good garden performance, to resist leaf scorching under full sunlight conditions and to tolerate rain, wind and temperatures ranging from about −20° C. to about 38° C.

It is claimed:

1. A new and distinct *Buddleja* plant named 'BUDHUR99' as illustrated and described.

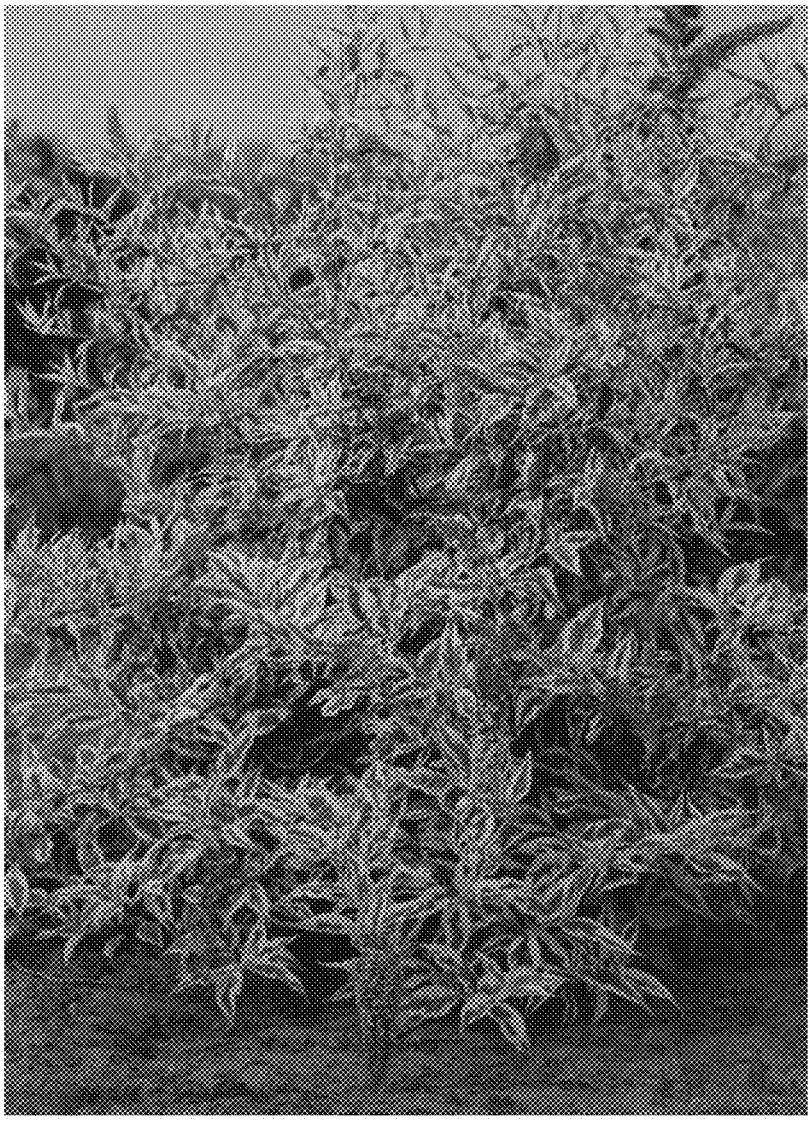

* * * * *